United States Patent [19]

Hanayama et al.

[11] Patent Number: 4,982,010
[45] Date of Patent: Jan. 1, 1991

[54] METHOD OF PRODUCING 4-BIPHENYL P-TOLYL ETHER

[75] Inventors: Naoki Hanayama, Oita; Kazuo Nakagawa, Mie; Akira Shimada, Osaka, all of Japan

[73] Assignee: Yoshitomi Pharmaceutical Industries, Ltd., Osaka, Japan

[21] Appl. No.: 429,433

[22] Filed: Oct. 31, 1989

[51] Int. Cl.$^5$ ............................................. C07C 41/00
[52] U.S. Cl. ................................................... 568/635
[58] Field of Search ....................................... 568/635

[56] References Cited

U.S. PATENT DOCUMENTS

| | | | |
|---|---|---|---|
| 1,882,368 | 10/1932 | Marschner et al. | 568/635 |
| 3,914,298 | 10/1975 | Dahl | 568/635 |
| 4,288,386 | 9/1981 | Soula et al. | |
| 4,694,110 | 9/1987 | Takenaka et al. | 568/638 |

FOREIGN PATENT DOCUMENTS

| | | |
|---|---|---|
| 0289041 | 4/1988 | European Pat. Off. |
| 1160935 | 6/1989 | Japan |
| 7806111 | 12/1978 | Netherlands |

*Primary Examiner*—Paul J. Killos
*Attorney, Agent, or Firm*—Sughrue, Mion, Zinn, MacPeak & Seas

[57] ABSTRACT

The use of 1,3-dimethyl-2-imidazolidinone or sulfolane as a reaction promoter is effective in the production of 4-biphenylyl p-tolyl ether, which is useful as a sensitizer for heat-sensitive recording paper, by reacting p-phenylphenol with a p-halotoluene in the presence of a copper catalyst.

5 Claims, No Drawings

METHOD OF PRODUCING 4-BIPHENYL P-TOLYL ETHER

FIELD OF THE INVENTION

The present invention relates to an industrially advantageous method of producing 4-biphenylyl p-tolyl ether, which is useful as a sensitizer for use in heat-sensitive recording paper.

BACKGROUND OF THE INVENTION

Laid-open European Patent Application No. 289,041 discloses that 4-biphenylyl p-tolyl ether having the formula (I):

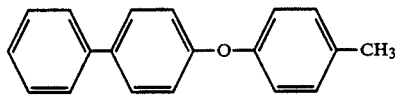 (I)

is useful as a sensitizer for use in heat-sensitive recording paper and that it can be prepared in 80% yield by reacting p-phenylphenol with p-bromotoluene in the presence of a copper powder and recovering the reaction product from a toluene extract.

According to Japanese Patent Publication No. 451/1981, 4-biphenylyl p-tolyl ether can be obtained in 76% yield by reacting p-phenylphenol with p-chlorotoluene in the presence of a catalyst mixture composed of a copper chloride compound, a copper powder and activated alumina and in the presence of dimethylacetamide.

Furthermore, Japanese Kokai Tokkyo Koho No. 257938/1986 discloses the use of 1,3-dimethyl-2-imidazolidinone or sulfolane as a polar solvent in producing m-phenoxybenzyl alcohol by reacting chlorobenzene with m-hydroxybenzyl alcohol in the presence of a copper compound catalyst and a base.

For the production of diaryl ethers, such as 4-biphenylyl p-tolyl ether, the so-called Ullmann reaction is known, according to which a hydroxyarene metal salt is reacted with an aryl halide in the, presence of a copper catalyst. In said Ullmann reaction, aryl bromides, which are highly reactive, are generally used as the aryl halide, as described in Laid-open European Patent Application No. 289,04. However, aryl bromides are expensive and their use in commercial-scale production is disadvantageous from the economical viewpoint. On the other hand, aryl chlorides are very inexpensive, although they are much inferior in reactivity to aryl bromides. Therefore, the use of aryl chlorides is preferred from the commercial viewpoint.

As described in Japanese Patent Publication No. 451/1981, however, a long reaction period is required and the yield is unsatisfactory from the commercial viewpoint even when dimethylacetamide is used as a promoter. While it is known that N,N-dimethylformamide, N-methyl-2-pyrrolidone, dimethyl sulfoxide, hexamethylphosphoramide, diethylene glycol alkyl ethers and the like can serve as reaction promoters in the Ullmann reaction, the use of these in the reaction of p-phenylphenol and p-chlorotoluene has failed to give 4-biphenylyl p-tolyl ether in commercially satisfactory yields.

According to Japanese Kokai Tokkyo Koho No. 257938/1986, the desired yield increase can be attained only under very strictly specified conditions, namely by using 1,3-dimethyl-2-imidazolidinone or sulfolane as a solvent in large amounts selected properly in relation to the starting materials and removing the byproduct water azeotropically with one of the starting materials within an appropriate temperature range. It is difficult to apply such a complicated reaction procedure to a reaction involving different starting materials.

Accordingly, it is an object of the invention to provide a method of producing 4-biphenylyl p-tolyl ether in a commercially advantageous manner.

SUMMARY OF THE INVENTION

The present invention thus provides an industrially advantageous method of producing 4-biphenylyl p-tolyl ether in markedly increased yields by using 1,3-dimethyl-2-imidazolidinone or sulfolane as a reaction promoter.

DETAILED DESCRIPTION OF THE INVENTION

The method according to the invention comprises reacting p-phenylphenol with a toluene compound of the general formula (II):

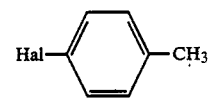 (II)

wherein Hal is a halogen atom, in the presence of a copper catalyst and in the presence of 1,3-dimethyl-2-imidazolidinone or sulfolane as a reaction promoter to give 4-biphenylyl p-tolyl ether of the formula (I):

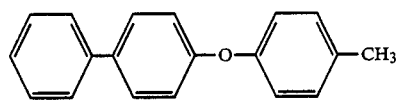 (I)

The compounds of general formula (II) which are to be used in the practice of the invention include p-chlorotoluene, p-bromotoluene and p-iodotoluene. Particularly preferred is p-chlorotoluene, however.

In the practice of the invention, it is preferable to react p-phenylphenol with p-chlorotoluene. The toluene compound is preferably used in an amount at least equimolar to p-phenylphenol, more preferably within the range of 1 to 10 moles per mole of p-phenylphenol. In the case of p-chlorotoluene, the use of 1.0 to 1.6 moles of p-chlorotoluene per mole of p-phenylphenol is sufficient when an inert solvent, such as toluene or xylene, is used. It is also possible to use p-chlorotoluene itself as a solvent and, in that case, it is used in further excess. The other starting material, namely p-phenylphenol, may be used in the form of a metal salt. An alkali metal salt is preferred as the metal salt. The alkali metal salt can be prepared by reacting p-phenylphenol with an alkali metal alkoxide (e.g., potassium methoxide, sodium methoxide, potassium ethoxide, sodium ethoxide, potassium tert-butoxide), an alkali metal hydroxide (e.g. potassium hydroxide, sodium hydroxide), an alkali metal carbonate (e.g. potassium carbonate, sodium carbonate), an alkali metal hydrogen carbonate (e.g. potassium hydrogen carbonate, sodium hydrogen carbonate) or the like alkali metal salt forming agent. It is not always necessary to isolate the alkali metal salt thus formed prior to the condensation reaction. From the commercial viewpoint, it is advantageous to charge a reactor with p-phenylphenol and an alkali metal salt forming agent and, after alkali metal salt formation, carry out the condensation reaction with the toluene compound in the same reactor. The alkali metal salt forming agent is used generally in an amount of 0.9 to 2.0 alkali equivalents, preferably 0.95 to 1.5 alkali equivalents, per mole of p-phenylphenol.

The reaction promoter, namely 1,3-dimethyl-2-imidazolidinone or sulfolane, is preferably used in an amount within the range of 0.5 to 30 percent by weight based on p-phenylphenol.

The copper catalyst includes, among others, copper powder, copper halides (e.g., copper chloride), copper carbonate, copper oxide (e.g., cuprous oxide or cupric oxide), copper salts of organic carboxylic acids (e.g., copper naphthenate) and copper complex catalysts (e.g., 8-hydroxyquinoline-copper complex,) acetylacetone-copper complex; prepared separately or prepared in situ by charging the reactor with an inorganic copper compound, such as copper chloride, and 8-hydroxyquinoline, acetylacetone or the like for copper complex catalyst formation. The amount of such copper catalyst may vary depending on the starting materials, reaction temperature, reaction period and other factors. Generally, however, the copper catalyst is used in an amount of 0.01 to 10 percent by weight, preferably 0.1 to 3.0 percent by weight, based on the biphenyl compound of general formula (I).

The reaction is generally carried out at a temperature of 120° to 280° C., preferably at 140° to 200° C., at ordinary pressure for 5 to 29 hours with stirring. In cases where an alkali metal salt of p-phenylphenol is formed in advance by reacting the starting material p-phenylphenol with an alkali metal salt forming agent, water is formed in the reaction system, and it is advisable to charge the reactor first with other reactants than the catalyst, heat the charge under reflux, remove the water resulting from azeotropic distillation from the system, then add the catalyst and let the reaction start. It is also possible to carry out the reaction by charging the reactor with all reactants, inclusive of the catalyst, and allow the reaction to proceed with heating under reflux while the distillate water resulting from azeotropic distillation is taken out of the system.

After completion of the reaction, the desired product can be isolated and purified by conventional means, such as washing with water, solvent removal by distillation, distillation and recrystallization, used either singly or in combination.

In accordance with the invention, the desired product, namely 4-biphenylyl p-tolyl ether, which is useful as a sensitizer for heat-sensitive recording paper, can be produced at a lower temperature, in a shorter time and in a higher yield as compared with the prior art methods by using, as a reaction promoter, 1,3-dimethyl -2-imidazolidinone or sulfolane, which has so far been known to serve as a solvent for the production of specific diaryl ethers only under strictly specified conditions of use.

The following examples are further illustrative of the present invention but by no means limitative of the scope thereof.

EXAMPLE 1

A four-necked flask equipped with a thermometer, a stirrer, and a reflux condenser with a water trap was charged with 554.7 g of p-phenylphenol, 607.7 g of p-chlorotoluene, 265.4 g of potassium carbonate, 8.0 g of 8-hydroxyquinoline-copper complex and 82 g of 1,3-dimethyl-2-imidazolidinone. The mixture was stirred at 140° to 180° C. under nitrogen for 5 hours while the temperature was raised gradually. The material which was collected in the trap was removed from time to time. After 15 hours of further heating at 170° to 185°C. with stirring, the ratio of p-phenylphenol and 4-biphenylyl p-tolyl ether in the reaction mixtures was found to be 1.5:98.5 as determined by GLC (gas-liquid chromatography) on the area ratio basis. Thereafter, the resulting mixture was concentrated under reduced pressure (10 mmHg) to give 270 g of a distillate composed of p-chlorotoluene and 1,3-dimethyl-2-imidazolidinone. Toluene (400 ml) was added to the residue for dissolving the reaction product. The organic layer was washed with a 10% sodium hydroxide solution, 10% sulfuric acid, and water, in that order. The toluene was then distilled off under reduced pressure to give 796 g of crude, light brown 4-biphenylyl p-tolyl ether in 95% yield. Distillation of the crude product under reduced pressure (2 mmHg) at 190° to 195° C. to give 775 g (92% yield) of white 4-biphenylyl p-tolyl ether melting at 97° to 99° C.

EXAMPLE 2

A mixture of 340 g of p-phenylphenol, 630 g of p-chlorotoluene, 68 g of 1,3-dimethyl-2-imidazolidinone and 81.0 g of sodium hydroxide was stirred at 160° to 168° C., and the water was separated azeotropically was removed by means of a trap. After adding 5.0 g of 8-hydroxyquinoline-copper complex, the mixture was further stirred at 155° to 165° C. for 15 hours. GLC analysis showed that the conversion of p-phenylphenol to the desired product was 98%. The same after treatment as in Example 1 gave 490 g of a crude product in 94% yield. It was dissolved in isopropyl alcohol, decolorized with active carbon and clay, and recrystallized to give 4-biphenylyl p-tolyl ether as white crystals melting at 97° to 98° C.

EXAMPLE 3

A mixture of 34.0 g of p-phenylphenol, 50.6 g of p-chlorotoluene, 16.6 g of potassium carbonate, 6.8 g of 1,3-dimethyl-2-imidazolidinone and 0.5 g of acetylacetone-copper complex was stirred at 140° to 180° C. for 4 hours, while the distillate water was removed from time to time. The mixture was further stirred at 170° to 185° C. for 15 hours. The conversion of p-phenylphenol to 4-biphenylyl p-tolyl ether was 95.2% (GLC analysis).

EXAMPLE 4

The procedure of Example 3 was followed except that 1.5 g of cuprous chloride was used instead of acetylacetone-copper complex. After 20 hours of stirring at 180° to 220° C. following the water-removing step, the conversion of p-phenylphenol to 4-biphenylyl p-tolyl ether was 93.2%.

EXAMPLE 5

A mixture of 200 g of p-phenylphenol, 400 g of p-chlorotoluene, 30 g of 1,3-dimethyl-2-imidazolidinone and 47 g of sodium hydroxide was stirred at 140° to 165° C. under nitrogen, while the distillate water was removed from time to time. After adding 4 g of copper naphthenate, the mixture was further stirred at 165° to 180° C. for 15 hours. The conversion of p-phenylphenol to 4-biphenylyl p-tolyl ether amounted to 97.5% (GLC analysis).

EXAMPLE 6

A mixture of 200 g of p-phenylphenol, 400 g of p-chlorotoluene, 30 g of 1,3-dimethyl-2-imidazolidinone and 69 g of 95% potassium hydroxide was stirred at 140° to 165° C. under nitrogen while the distillate water was removed from time to time. After adding 2 g of cupric oxide, the mixture was further stirred at 165° to 180° C. for 12 hours. The conversion of p-phenylphenol to 4bi-phenylyl p-tolyl ether was 96.0% (GLC analysis). EXAMPLE 7

A mixture of 200 g of p-phenylphenol, 400 g of p-chlorotoluene, 40 g of sulfolane and 69 g of 95% potassium hydroxide was stirred at 140° to 170° C. under nitrogen, while the distillate water was removed from time to time. After adding 3 g of 8-hydroxyquinoline-copper complex, the mixture was further stirred at 165° to 180° C. for 15 hours. The conversion of p-phenylphenol to 4-biphenylyl p-tolyl ether was 97.2% (GLC analysis).

COMPARATIVE EXAMPLE 1

A mixture of 34.0 g of p-phenylphenol, 50.6 g of p-chlorotoluene, 16.6 g of potassium carbonate, 0.5 g of 8-hydroxyquinoline-copper complex and 17 g of dimethyl sulfoxide was stirred at 170° to 185° C. for 20 hours, while the distillate water was removed from time to time. The conversion was 84.2%.

COMPARATIVE EXAMPLE 2

The procedure of Comparative Example 1 was repeated except that 17 g of diethylene glycol dibutyl ether was used instead of dimethyl sulfoxide. The conversion was 78.5%.

COMPARATIVE EXAMPLE 3

The procedure of Comparative Example 1 was repeated except that the use of dimethyl sulfoxide was omitted. The conversion was 74.6%.

While the present invention has been described by the foregoing specification including working examples and test examples, the embodiment described herein can be changed and modified in various manners within the scope and the spirit of this invention.

What is claimed is:

1. A method of producing 4-biphenylyl p-tolyl ether of the formula (I):

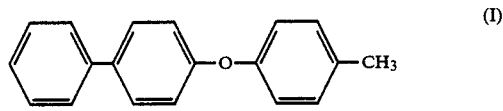

which comprises reacting p-phenylphenol with a toluene compound of the general formula (II):

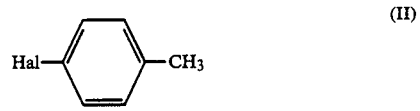

wherein Hal is a halogen atom, in the presence of a copper catalyst and in the presence of 1,3-dimethyl-2-imidazolidinone or sulfolane as a reaction promoter.

2. A method as claimed in claim 1, wherein p-phenylphenol is used in the form of a metal salt.

3. A method as claimed in claim 2, wherein the metal salt is an alkali metal salt.

4. A method as claimed in claim 1, wherein the toluene compound is p-chlorotoluene.

5. A method as claimed in claim 1, wherein the reaction promoter, namely 1,3-dimethyl-2-imidazolidinone sulfolane, is used in an amount of 0.5 to 30 percent by weight based on p-phenylphenol.

* * * * *